US008969060B2

(12) United States Patent
Honda et al.

(10) Patent No.: US 8,969,060 B2
(45) Date of Patent: Mar. 3, 2015

(54) MODIFIED GLUCOSE DEHYDROGENASE

(75) Inventors: Michinari Honda, Hiroshima (JP);
Tsuyoshi Kameda, Hiroshima (JP);
Fuminao Kobayashi, Hiroshima (JP)

(73) Assignee: Ikeda Food Research Co., Ltd.,
Fukuyama-Shi, Hiroshima (JP)

( * ) Notice: Subject to any disclaimer, the term of this patent is extended or adjusted under 35 U.S.C. 154(b) by 126 days.

(21) Appl. No.: 13/598,944

(22) Filed: Aug. 30, 2012

(65) Prior Publication Data

US 2013/0065261 A1  Mar. 14, 2013

(30) Foreign Application Priority Data

Sep. 9, 2011  (JP) .................. 2011-197216

(51) Int. Cl.
*C12N 9/04* (2006.01)
*C12Q 1/32* (2006.01)
*C07K 14/00* (2006.01)
*C12P 21/00* (2006.01)

(52) U.S. Cl.
CPC .......... *C12N 9/0006* (2013.01); *C12Y 101/9901* (2013.01)
USPC ............. 435/190; 435/26; 435/69.1; 530/350

(58) Field of Classification Search
CPC ...... C12N 9/0006; C12N 9/0004; C12Q 1/32; C12Q 1/006; C12Q 1/004; C12Q 1/54; C12Y 101/9901; A61B 5/14532; A61B 5/1486; G01N 2333/902; G01N 33/66
USPC ................... 435/190, 69.1; 530/350
See application file for complete search history.

(56) References Cited

U.S. PATENT DOCUMENTS 8,445,221 B2 * 5/2013 Honda et al. ................ 435/14
2003/0203973 A1 10/2003 Cooper et al.
2004/0013575 A1 1/2004 Stevens et al.
2006/0063217 A1 3/2006 Omura et al.
2010/0323378 A1 12/2010 Honda et al.
2012/0122130 A1 5/2012 Omura et al.

FOREIGN PATENT DOCUMENTS

JP           4496407      7/2010
JP        2010-275216    12/2010
JP        2011-147437     8/2011
WO   WO 2009/084616  *  7/2009

OTHER PUBLICATIONS

Witkowski et al., Biochemistry 38:11643-11650, 1999.*
Branden et al., Introduction to Protein Structure, Garland Publishing Inc., New York, p. 247, 1991.*
Seffernick et al., J. Bacteriol. 183(8):2405-2410, 2001.*

* cited by examiner

Primary Examiner — Delia Ramirez
(74) Attorney, Agent, or Firm — Wenderoth, Lind & Ponack, L.L.P.

(57) ABSTRACT

The purpose of the present invention is to provide an FAD-conjugated glucose dehydrogenase that is hard to be inhibited by the inhibitors such as 1,10-phenanthroline.

The present invention relates to a modified glucose dehydrogenase (GLD), comprising an amino acid sequence of a wild-type FAD-conjugated glucose dehydrogenase (GLD) represented by SEQ ID NO: 1 having a substitution of at least one amino acid residue selected from the group consisting of amino acid residues at positions 298, 338, 340, 341, 343, 352, 354, 424, 426, 431 and 432, wherein the modified GLD has a reduced susceptibility to an inhibitor, as compared with the wild-type GLD, especially to said modified GLD, which has 40% or more of a relative activity when determined in a system wherein the inhibitor coexists at a final concentration of 1 mM based on an enzymatic activity when determined in a system wherein the inhibitor does not coexist.

11 Claims, 4 Drawing Sheets

SEQUENCE LISTING

```
<160> NUMBER OF SEQ ID NOS: 17

<210> SEQ ID NO 1
<211> LENGTH: 592
<212> TYPE: PRT
<213> ORGANISM: Aspergillus terreus
<220> FEATURE:
<221> NAME/KEY: SIGNAL
<222> LOCATION: (1)..(19)
<223> OTHER INFORMATION:

<400> SEQUENCE: 1

Met Leu Gly Lys Leu Ser Phe Leu Ser Ala Leu Ser Leu Ala Val Ala
1               5                   10                  15

Ala Pro Leu Ser Asn Ser Thr Ser Ala Lys Tyr Asp Tyr Ile Val Ile
                20                  25                  30

Gly Gly Gly Thr Ser Gly Leu Ala Val Ala Asn Arg Leu Ser Glu Asp
            35                  40                  45

Pro Asn Val Asn Val Leu Ile Leu Glu Ala Gly Gly Ser Val Trp Asn
    50                  55                  60

Asn Pro Asn Val Thr Asn Val Asp Gly Tyr Gly Leu Ala Phe Gly Ser
65                  70                  75                  80

Asp Ile Asp Trp Gln Tyr Gln Ser Val Asn Gln Pro Tyr Gly Gly Asn
                85                  90                  95

Leu Ser Gln Val Leu Arg Ala Gly Lys Ala Leu Gly Gly Thr Ser Thr
            100                 105                 110

Ile Asn Gly Met Ala Tyr Thr Arg Ala Glu Asp Val Gln Ile Asp Ala
        115                 120                 125

Trp Glu Thr Ile Gly Asn Thr Gly Trp Thr Trp Lys Asn Leu Phe Pro
    130                 135                 140

Tyr Tyr Arg Lys Ser Glu Asn Phe Thr Val Pro Thr Lys Ser Gln Thr
145                 150                 155                 160

Ser Leu Gly Ala Ser Tyr Glu Ala Gly Ala His Gly His Glu Gly Pro
                165                 170                 175

Leu Asp Val Ala Phe Thr Gln Ile Glu Ser Asn Asn Leu Thr Thr Tyr
            180                 185                 190

Leu Asn Arg Thr Phe Gln Gly Met Gly Leu Pro Trp Thr Glu Asp Val
        195                 200                 205

Asn Gly Gly Lys Met Arg Gly Phe Asn Leu Tyr Pro Ser Thr Val Asn
    210                 215                 220

Leu Glu Glu Tyr Val Arg Glu Asp Ala Ala Arg Ala Tyr Tyr Trp Pro
225                 230                 235                 240

Tyr Lys Ser Arg Pro Asn Leu His Val Leu Leu Asn Thr Phe Ala Asn
                245                 250                 255
```

```
Arg Ile Val Trp Asp Gly Glu Ala His Asp Gly His Ile Thr Ala Ser
            260                 265                 270

Gly Val Glu Ile Thr Ser Arg Asn Gly Thr Val Arg Val Ile Asn Ala
        275                 280                 285

Glu Lys Glu Val Ile Val Ser Ala Gly Ala Leu Lys Ser Pro Ala Ile
    290                 295                 300

Leu Glu Leu Ser Gly Ile Gly Asn Pro Ser Val Leu Asp Lys His Asn
305                 310                 315                 320

Ile Pro Val Lys Val Asn Leu Pro Thr Val Gly Glu Asn Leu Gln Asp
                325                 330                 335

Gln Val Asn Ser His Met Asp Ala Ser Gly Asn Thr Ser Ile Ser Gly
            340                 345                 350

Thr Lys Ala Val Ser Tyr Pro Asp Val Tyr Asp Val Phe Gly Asp Glu
        355                 360                 365

Ala Glu Ser Val Ala Lys Gln Ile Arg Ala Asn Leu Lys Gln Tyr Ala
    370                 375                 380

Ala Asp Thr Ala Lys Ala Asn Gly Asn Ile Met Lys Ala Ala Asp Leu
385                 390                 395                 400

Glu Arg Leu Phe Glu Val Gln Tyr Asp Leu Ile Phe Lys Gly Arg Val
                405                 410                 415

Pro Ile Ala Glu Val Leu Asn Tyr Pro Gly Ser Ala Thr Ser Val Phe
            420                 425                 430

Ala Glu Phe Trp Ala Leu Leu Pro Phe Ala Arg Gly Ser Val His Ile
        435                 440                 445

Gly Ser Ser Asn Pro Ala Glu Phe Pro Val Ile Asn Pro Asn Tyr Phe
    450                 455                 460

Met Leu Asp Trp Asp Ala Lys Ser Tyr Val Ala Val Ala Lys Tyr Ile
465                 470                 475                 480

Arg Arg Ser Phe Glu Ser Tyr Pro Leu Ser Ser Ile Val Lys Glu Ser
                485                 490                 495

Thr Pro Gly Tyr Asp Val Ile Pro Arg Asn Ala Ser Glu Gln Ser Trp
            500                 505                 510

Lys Glu Trp Val Phe Asp Lys Asn Tyr Arg Ser Asn Phe His Pro Val
        515                 520                 525

Gly Thr Ala Ala Met Met Pro Arg Glu Ile Gly Gly Val Val Asp Glu
    530                 535                 540

Arg Leu Asn Val Tyr Gly Thr Thr Asn Val Arg Val Val Asp Ala Ser
545                 550                 555                 560

Val Leu Pro Phe Gln Val Cys Gly His Leu Val Ser Thr Leu Tyr Ala
                565                 570                 575

Val Ala Glu Arg Ala Ala Asp Leu Ile Lys Ala Asp Ala Gly Arg Arg
            580                 585                 590

<210> SEQ ID NO 2
<211> LENGTH: 1779
<212> TYPE: DNA
<213> ORGANISM: Aspergillus terreus
<220> FEATURE:
<221> NAME/KEY: sig_peptide
<222> LOCATION: (1)..(57)
<223> OTHER INFORMATION:

<400> SEQUENCE: 2
atgttgggaa agctctcctt cctcagtgcc ctgtccctgg cagtggcggc acctttgtcc     60
aactccacgt ccgccaaata tgattatatc gttattggag gcggtactag cggtttggcc    120
```

```
gtcgcaaacc gtctatcgga ggatccaaac gtgaacgtac tcattctgga ggccggtggc      180
tcggtctgga acaatcccaa tgtcacaaac gtggatggct acgggcttgc ttttgggtct      240
gacattgact ggcaatacca gtccgtcaac cagccatatg gaggcaacct tagtcaagtg      300
cttcgtgccg gcaaggccct tggtggtact agtactatca atggcatggc ctatacgcgc      360
gccgaggatg tccagatcga cgcctgggaa accattggca acacaggatg gacgtggaag      420
aatctgttcc cttactatcg gaagagcgag aactttactg tccctaccaa atcgcagacc      480
tctcttggag cgtcgtatga agctggagcc cacggccacg agggtcccct tgacgttgcc      540
ttcactcaga tcgagtcgaa caacctgacc acttacctca accgtacctt ccagggcatg      600
ggactcccat ggacggagga cgtcaatggc ggaaagatgc gcggctttaa cttataccccc     660 tccaccgtga atcttgagga gtatgtgcgc gaagacgccg ctcgtgcata ctactggccc      720
tacaagtccc gtcccaactt gcatgtcctg ctcaacactt tgccaaccg gattgtgtgg       780 gacggcgaag cccatgacgg ccacatcact gccagtggtg tcgagatcac ttccaggaac      840
ggcactgttc gtgttatcaa tgcggagaag gaagtcattg tctctgccgg tgccttgaag      900
tccccggcta ccttgaact ttctggaatt ggcaaccca gcgttcttga caagcacaac        960
atccccgtca aggtcaacct cccgactgtc ggcgagaacc ttcaggacca agtgaacagc      1020
cacatggatg catcgggcaa cacttccatc tctggaacca aggcagtctc ctaccccgat      1080
gtctatgacg tcttcggtga cgaagccgag tcggtcgcca acagatccg tgccaacctg       1140 aagcaatacg ccgccgacac cgccaaggcc aacggaaaca ttatgaaggc cgccgatctg      1200
gagcgtctct tcgaggtcca gtatgacctt atttcaagg gcagagttcc aatcgctgaa       1260
gtcctgaact atccgggcag cgcgacgtcc gtgtttgcag aattctgggc cctccttccc      1320
ttcgctcgtg gaagtgttca catcggttct tcaaacccgg ccgagttccc tgtcatcaac      1380
cccaactatt tcatgctcga ctgggacgcg aagagctacg ttgccgttgc gaagtatatc      1440
cgccgttcgt tcgagagcta ccctctcagc agtatcgtga aggagtctac ccctggctat      1500
gatgttatcc cccggaacgc ttctgagcag agctggaaag aatgggtctt tgataagaac      1560
tatcgttcta acttccatcc cgtcggcacg gctgccatga tgcctcgtga gattggtggt      1620
gtcgtggacg agcgtctgaa tgtctatggc actacgaatg tcagagttgt agatgcttcg      1680
gtccttccat tccaggtctg cggccatttg gtgagcacac tatacgctgt ggccgaacgg      1740
gcggcggatc tcatcaaggc cgatgctggt cgtcgttag                             1779
```

<210> SEQ ID NO 3
<211> LENGTH: 39
<212> TYPE: DNA
<213> ORGANISM: Artificial Sequence
<220> FEATURE:
<223> OTHER INFORMATION: Primer

<400> SEQUENCE: 3

```
ggcagatctt ccaactccac gtccgccaaa tatgattat                             39
```

<210> SEQ ID NO 4
<211> LENGTH: 48
<212> TYPE: DNA
<213> ORGANISM: Artificial Sequence
<220> FEATURE:
<223> OTHER INFORMATION: Primer

<400> SEQUENCE: 4

```
ctgcaggtcg acgcatgcct aacgacgacc agcatcggcc ttgatgag                   48
```

<210> SEQ ID NO 5
<211> LENGTH: 39
<212> TYPE: DNA
<213> ORGANISM: Artificial Sequence
<220> FEATURE:
<223> OTHER INFORMATION: Primer

<400> SEQUENCE: 5
ggcagatctt ccaactccac gtccgccaaa tatgattat                                39

<210> SEQ ID NO 6
<211> LENGTH: 46
<212> TYPE: DNA
<213> ORGANISM: Artificial Seqeunce
<220> FEATURE:
<223> OTHER INFORMATION: Primer

<400> SEQUENCE: 6
acatgcatgc tctagactaa cgacgaccag catcggcctt gatgag                        46

<210> SEQ ID NO 7
<211> LENGTH: 39
<212> TYPE: DNA
<213> ORGANISM: Artificial Sequence
<220> FEATURE:
<223> OTHER INFORMATION: Primer

<400> SEQUENCE: 7
ggcagatctt ccaactccac gtccgccaaa tatgattat                                39

<210> SEQ ID NO 8
<211> LENGTH: 46
<212> TYPE: DNA
<213> ORGANISM: Artificial Seqeunce
<220> FEATURE:
<223> OTHER INFORMATION: Primer

<400> SEQUENCE: 8
acatgcatgc tctagactaa cgacgaccag catcggcctt gatgag                        46

<210> SEQ ID NO 9
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(16)
<223> OTHER INFORMATION: any

<400> SEQUENCE: 9
tgtctctgcc ggtnnnttga agtccccggc                                          30

<210> SEQ ID NO 10
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (15)..(17)
<223> OTHER INFORMATION: any

<400> SEQUENCE: 10
aggaccaagt gaacnnncac atggatgcat                                           30

<210> SEQ ID NO 11
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(16)
<223> OTHER INFORMATION: any

<400> SEQUENCE: 11
ccaagtgaac agcnnnatgg atgcatcggg                                           30

<210> SEQ ID NO 12
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(16)
<223> OTHER INFORMATION: any

<400> SEQUENCE: 12
gaacagccac atgnnngcat cgggcaacac                                           30

<210> SEQ ID NO 13
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(16)
<223> OTHER INFORMATION: any

<400> SEQUENCE: 13
cacttccatc tctnnnacca aggcagtctc                                           30

<210> SEQ ID NO 14
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(16)
<223> OTHER INFORMATION: any

<400> SEQUENCE: 14
catctctgga accnnngcag tctcctaccc                                           30

<210> SEQ ID NO 15
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(16)
<223> OTHER INFORMATION: any

<400> SEQUENCE: 15

```
<210> SEQ ID NO 16
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(16)
<223> OTHER INFORMATION: any

<400> SEQUENCE: 16
cagcgcgacg tccnnntttg cagaattctg                                30

<210> SEQ ID NO 17
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(16)
<223> OTHER INFORMATION: any

<400> SEQUENCE: 17
cgcgacgtcc gtgnnngcag aattctgggc                                30
```

US 8,969,060 B2

MODIFIED GLUCOSE DEHYDROGENASE

TECHNICAL FIELD

The present invention relates to an FAD-conjugated glucose dehydrogenase (GLD) which requires flavin adenine dinucleotide (FAD) as a coenzyme and catalyzes a reaction of the dehydrogenation (oxidation) of a hydroxy group at the 1-position of glucose. More particularly, the invention relates to a modified GLD polypeptide having a reduced susceptibility to 1,10-phenanthroline; a polynucleotide encoding the modified GLD; a method for the production of the enzyme; and a method for the determination of glucose, a reagent composition for use in the determination of glucose, a biosensor for use in the determination of glucose, and others, each characterized by using the enzyme. Incidentally, in the description, unless otherwise specified, monosaccharides such as glucose refer to those in the D-form.

BACKGROUND ART

The blood glucose concentration is an important marker for diabetes. In the determination of a blood glucose concentration, a glucose oxidase has conventionally been used. However, such a glucose oxidase is affected by a dissolved oxygen concentration and an error is caused in the measured value. Therefore, a glucose dehydrogenase which is not affected by oxygen has also been widely used recently.

As a commercially available glucose dehydrogenase which is not affected by oxygen, a glucose dehydrogenase which requires pyrroloquinoline quinone (PQQ) as a coenzyme (PQQ-GDH) is known, however, a conventional PQQ-GDH has a disadvantage that it reacts also with sugars other than glucose such as maltose and galactose.

As a countermeasure against this disadvantage, the group of the present inventors found a novel soluble GLD which requires FAD as a coenzyme from *Aspergillus terreus* FERM BP-08578 strain (Patent documents 1 and 2). Such a GLD has unprecedented excellent properties that it is not affected by dissolved oxygen, oxidizes a hydroxy group at the 1-position of glucose, and has a low activity (enzymatic activity) for maltose and galactose.

On the other hand, Patent Document 3 disclosed a method for decreasing the risk of coronary artery diseases by administering 1,10-phenanthroline to a patient of diabetes, especially Type-II diabetes. Patent Document 4 discloses a method for arresting hemorrhage by inhibiting ADAM8, an agent of promoting blood circulation and inhibiting thrombus formation, or a method for inhibiting blood clotting by increasing said agent. 1,10-phenanthroline is listed as an agent for inhibiting ADM8. Patent Document 5 discloses an invention relating to a tube for collecting blood, characterized by comprising 1,10-phenanthroline and the like for inhibiting the decomposition of proteins in a blood sample. Accordingly, when the determination of glucose is performed by using as a sample the blood obtained from a diabetes patient who has been treated with the methods disclosed in Patent Document 3 or 4, or by using as a sample the blood kept in the tube disclosed in Patent Document 5, there will be a possibility that a false blood glucose value might be determined due to the existence of 1,10-phenanthroline in said blood causing a risk that a wrong treatment would be adopted for the patient, if an enzyme contained in a device for the determination of blood glucose is affected by 1,10-phenanthroline.

Patent document 1: WO 2004/058958 pamphlet
Patent document 2: WO 2006/101239 pamphlet
Patent document 3: WO 2003/077901 pamphlet
Patent document 4: JP 2010-275216 A
Patent Document 5: Japanese Patent No. 4496407

DISCLOSURE OF THE INVENTION

Problems to be Solved by the Invention

As the conventional GLDs are affected by the inhibitors such as 1,10-phenanthroline, there is a need for a new GLD that is hard to be inhibited by the inhibitors. Accordingly, it is an object of the present invention to provide such GLD.

Means for Solving the Problems

The present invention will solve the above problems by providing a modified GLD enzyme (polypeptide) that is hard to be inhibited by the inhibitors such as 1,10-phenanthroline; a polynucleotide (gene) encoding the modified GLD; a method for the production of the enzyme by using a cell transformed with the gene; and a method for the determination of glucose, a reagent composition for use in the determination of glucose, a biosensor for use in the determination of glucose, and others, each characterized by using the enzyme.

The invention relates to the following aspects.

[Aspect 1]
A modified glucose dehydrogenase (GLD), comprising an amino acid sequence of a wild-type FAD-conjugated glucose dehydrogenase (GLD) represented by SEQ ID NO: 1 having a substitution of at least one amino acid residue selected from the group consisting of amino acid residues at positions 298, 338, 340, 341, 343, 352, 354, 424, 426, 431 and 432, wherein the modified GLD has a reduced susceptibility to an inhibitor, as compared with the wild-type GLD.

[Aspect 2]
A modified glucose dehydrogenase (GLD), comprising an amino acid sequence of a wild-type FAD-conjugated glucose dehydrogenase (GLD) represented by SEQ ID NO: 1 having a substitution of at least one amino acid residue selected from the group consisting of amino acid residues at positions 298 by aliphatic amino acid; 338 by sulfur-containing amino acids; 340 by an aliphatic, aromatic or acidic amino acid; 341 by an aliphatic, oxy, sulfur-containing, aromatic, acidic or basic amino acid, imino acid, or acidic amino acid amide; 343 by an aliphatic, oxy, sulfur-containing, aromatic, acidic or basic amino acid, or acidic amino acid amide; 352 by an aliphatic, oxy, sulfur-containing, aromatic, acidic or basic amino acid, imino acid, or acidic amino acid amide; 354 by an aliphatic, oxy, sulfur-containing, aromatic, acidic or basic amino acid, imino acid, or acidic amino acid amide; 424 by an aliphatic, oxy, sulfur-containing, acidic or basic amino acid, or acidic amino acid amide; 426 by an aliphatic, oxy, sulfur-containing, aromatic, acidic or basic amino acid, imino acid, or acidic amino acid amide; 431 by an aromatic amino acid; and 432 by an aliphatic, oxy, sulfur-containing or basic amino acid, or acidic amino acid amide, wherein the modified GLD has a reduced susceptibility to an inhibitor, as compared with the wild-type GLD.

[Aspect 3]
A modified glucose dehydrogenase (GLD), comprising an amino acid sequence of a wild-type FAD-conjugated glucose dehydrogenase (GLD) represented by SEQ ID NO: 1 having a substitution of an amino acid residue selected from the group consisting of:
A298I, A298V, V338M, S340G, S340N, S340V, S340W, H341A, H341C, H341D, H341E, H341F, H341G, H341I, H341K, H341L, H341M, H341N, H341P, H341Q, H341R, H341S, H341V, H341W, H341Y, D343A, D343E, D343F, D343H, D343I, D343K, D343L, D343M, D343N, D343Q, D343R, D343S, D343W, D343Y, D343V, G352A, G352C, G352D, G352E, G352F, G352I, G352K, G352L, G352M, G352N, G352P, G352Q, G352R, G352S, G352T, G352V, G352W, G352Y, K354A, K354C, K354D, K354E, K354F, K354G, K354H, K354M, K354N, K354P, K354Q, K354Y, K354R, K354S, Y424C, Y424D, Y424E, Y424K, Y424N, Y424Q, Y424R, Y424S, Y424T, Y424V, G426A, G426C, G426D, G426E, G426F, G426H, G426I, G426K, G426L, G426M, G426N, G426P, G426R, G426S, G426T, G426W, G426Y, G426V, V431F, F432I, F432K, F432L, F432M, F432Q, F432R, F432T and F432V, and any combination thereof, wherein the modified GLD has a reduced susceptibility to an inhibitor, as compared with the wild-type GLD.

[Aspect 4]

A modified glucose dehydrogenase (GLD), comprising an amino acid sequence of having 90% or more of identity with that of a wild-type FAD-conjugated glucose dehydrogenase (GLD) represented by SEQ ID NO: 1 having a substitution of an amino acid residue in terms of the position of the wild-type GLD selected from the group consisting of:
A298I, A298V, V338M, S340G, S340N, S340V, S340W, H341A, H341C, H341D, H341E, H341F, H341G, H341I, H341K, H341L, H341M, H341N, H341P, H341Q, H341R, H341S, H341V, H341W, H341Y, D343A, D343E, D343F, D343H, D343I, D343K, D343L, D343M, D343N, D343Q, D343R, D343S, D343W, D343Y, D343V, G352A, G352C, G352D, G352E, G352F, G352I, G352K, G352L, G352M, G352N, G352P, G352Q, G352R, G352S, G352T, G352V, G352W, G352Y, K354A, K354C, K354D, K354E, K354F, K354G, K354H, K354M, K354N, K354P, K354Q, K354Y, 354R, K354S, Y424C, Y424D, Y424E, Y424K, Y424N, Y424Q, Y424R, Y424S, Y424T, Y424V, G426A, G426C, G426D, G426E, G426F, G426H, G426I, G426K, G426L, G426M, G426N, G426P, G426R, G426S, G426T, G426W, G426Y, G426V, V431F, F432I, F432K, F432L, F 432M, F432Q, F432R, F432T and F432V, and any combination thereof, wherein the modified GLD has a reduced susceptibility to an inhibitor, as compared with the wild-type GLD.

[Aspect 5]

The modified GLD according to any one of Aspects 1 to 4, which has 40% or more of a relative activity when determined in a system wherein the inhibitor coexists at a final concentration of 1 mM based on an enzymatic activity when determined in a system wherein the inhibitor does not coexist.

[Aspect 6]

A modified glucose dehydrogenase (GLD), comprising an amino acid sequence of a wild-type FAD-conjugated glucose dehydrogenase (GLD) represented by SEQ ID NO: 1 having a substitution of amino acid residue(s) selected from the group consisting of:
A298I, S272T+A298V+A369T, V338M+Q382H, L250V+S340G+D399N, S340N, S340V, S340W, H341A, H341C, H341D, H341E, H341F, H341G, H341I, H341K, H341L, H341M, H341N, H341P, H341Q, H341R+G499S, H341S, H341V, H341W, H341Y, D343A, D343E+L562H, R250L+D343E+K494E, D343F, D343H, D343I, D343K, D343L, D343M, D343N+S490S, D343Q, D343R, D343S, D343W, D343Y, D343V, G352A, G352C, G352D, G352E, G352F, G352I, G352K, G352L, G352M, G352N, G352P, G352Q, G352R, G352S, G352T, G352V, G352W, G352Y, K354A, K354C, K354D, K354E, K354F, K354G, K354H, K354M, M342L+K354N, K354P, K354Q, K354Y, K354R, K354S, Y424C, Y424D, Y424E, Y424K, Y424N, Y424Q, Y424R, Y424S, Y424T, Y424V, G426A, G426C, G426D, G426E, G426F, G426H, G426I, G426K, G426L, G426M, G426N, G426P, G426R, G426S+A578V, G426T, G426W, G426Y, G426V, V431F, F432I, F432K, F432L, F432M, F432Q, F432R, F432T and F432V, and any combination thereof.

[Aspect 7]

A modified glucose dehydrogenase (GLD), comprising an amino acid sequence of having 90% or more of identity with that of a wild-type FAD-conjugated glucose dehydrogenase (GLD) represented by SEQ ID NO: 1 having a substitution of amino acid residue(s) in terms of the position of the wild-type GLD selected from the group consisting of:
A298I, S272T+A298V+A369T, V338M+Q382H, L250V+S340G+D399N, S340N, S340V, S340W, H341A, H341C, H341D, H341E, H341F, H341G, H341I, H341K, H341L, H341M, H341N, H341P, H341Q, H341R+G499S, H341S, H341V, H341W, H341Y, D343A, D343E+L562H, R250L+D343E+K494E, D343F, D343H, D343I, D343K, D343L, D343M, D343N+S490S, D343Q, D343R, D343S, D343W, D343Y, D343V, G352A, G352C, G352D, G352E, G352F, G352I, G352K, G352L, G352M, G352N, G352P, G352Q, G352R, G352S, G352T, G352V, G352W, G352Y, K354A, K354C, K354D, K354E, K354F, K354G, K354H, K354M, M342L+K354N, K354P, K354Q, K354Y, K354R, K354S, Y424C, Y424D, Y424E, Y424K, Y424N, Y424Q, Y424R, Y424S, Y424T, Y424V, G426A, G426C, G426D, G426E, G426F, G426H, G426I, G426K, G426L, G426M, G426N, G426P, G426R, G426S+A578V, G426T, G426W, G426Y, G426V, V431F, F432I, F432K, F432L, F432M, F432Q, F432R, F432T and F432V, and any combination thereof, wherein the modified GLD has a reduced susceptibility to an inhibitor, as compared with the wild-type GLD.

[Aspect 8]

The modified GLD according to any one of Aspects 1 to 7, wherein the inhibitor is 1,10-phenanthroline.

[Aspect 9]

A polynucleotide encoding the modified GLD according to any one of Aspects 1-4, 6 and 7.

[Aspect 10]

The polynucleotide according to Aspect 9, wherein the polynucleotide encoding the amino acid sequence of the wild-type FAD-conjugated glucose dehydrogenase (GLD) represented by SEQ ID NO: 1 has a base sequence represented by SEQ ID NO: 2.

[Aspect 11]

A recombinant vector, comprising the polynucleotide according to Aspect 9.

[Aspect 12]

A transformed cell, which is produced by using the recombinant vector according to Aspect 11.

[Aspect 13]

The transformed cell according to Aspect 12, which is *Escherichia coli*, yeast or *Aspergillus oryzae*.

[Aspect 14]

A method for the production of a modified GLD, characterized by comprising: culturing the transformed cell according to Aspect 12 or 13; and collecting a modified GLD from the resulting culture.

[Aspect 15]

A method for the determination of glucose, characterized by using the modified GLD according to Aspect 1 or a modified GLD obtained by the production method according to Aspect 14.

[Aspect 16]

A reagent composition for use in the determination of glucose, characterized by comprising the modified GLD according to Aspect 1 or the modified GLD obtained by the production method according to Aspect 14.

[Aspect 17]
A biosensor for use in the determination of glucose, characterized by using the modified GLD according to Aspect 1 or the modified GLD obtained by the production method according to Aspect 14.

Advantage of the Invention

By using the polynucleotide of the invention, a modified GLD having the reduced susceptibility to the inhibitors can be produced uniformly in a large amount by, for example, a recombinant DNA technique. The blood glucose can be more accurately determined by using the modified GLD.

BEST MODE FOR CARRYING OUT THE INVENTION

Figure 1A:
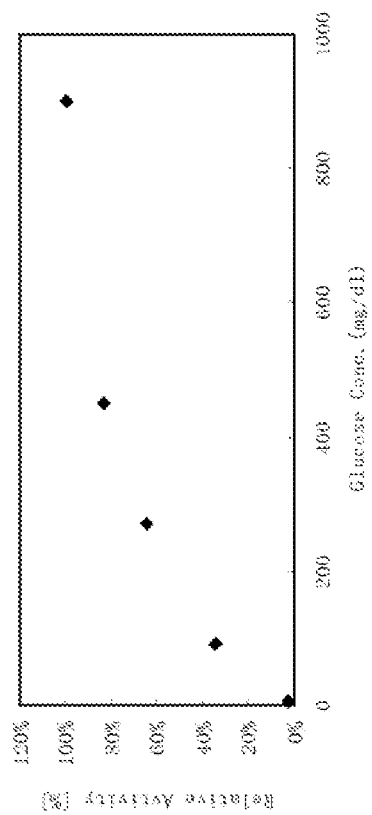
FIG. 1A shows a calibration curve for use in the determination of glucose obtained using a modified GLD "H341W" of the invention. X axis: Substrate concentration [mg/dL], Y axis: Relative activity [%]

An amino acid residue is described in the present specification with a one-letter abbreviation, such as "G" for glycine, "A" for alanine, "V" for valine, "L" for leucine, "I" for isoleucine, "F" for phenylalanine, "Y" for tyrosine, "W" for tryptophan, "S" for serine, "T" for threonine, "C" for cysteine, "M" for methionine, "D" for asparagic acid, "E" for glutamic acid, "N" for asparagine, "Q" for glutamine, "K" for lysine, "R" for arginine, "H" for histidine, and "P" for proline. The expression such as "S272T" means that serine(s) located at position 272 from a starting amino acid of methionine at position 1 in a particular amino acid sequence is substituted with threonine (T). Furthermore, the phrase "S272T+A298V+A369T" means that the amino-acid substitution has been simultaneously made at positions 272, 298 and 369, respectively.

The modified GLD of the invention is characterized by comprising a substitution of at least one amino acid residue selected from the group consisting of amino acid residues at positions 298, 338, 340, 341, 343, 352, 354, 424, 426, 431 and 432 in an amino acid sequence of a wild-type FAD-conjugated glucose dehydrogenase (GLD) represented by SEQ ID NO: 1, and having a reduced susceptibility to an inhibitor, as compared with the wild-type GLD.

The above substitution of the amino acid residues may be one at positions 298 by aliphatic amino acid; 338 by sulfur-containing amino acids; 340 by an aliphatic, aromatic or acidic amino acid; 341 by an aliphatic, oxy, sulfur-containing, aromatic, acidic or basic amino acid, imino acid, or acidic amino acid amide; 343 by an aliphatic, oxy, sulfur-containing, aromatic, acidic or basic amino acid, or acidic amino acid amide; 352 by an aliphatic, oxy, sulfur-containing, aromatic, acidic or basic amino acid, imino acid, or acidic amino acid amide; 354 by an aliphatic, oxy, sulfur-containing, aromatic, acidic or basic amino acid, imino acid, or acidic amino acid amide; 424 by an aliphatic, oxy, sulfur-containing, acidic or basic amino acid, or acidic amino acid amide; 426 by an aliphatic, oxy, sulfur-containing, aromatic, acidic or basic amino acid, imino acid, or acidic amino acid amide; 431 by an aromatic amino acid; and 432 by an aliphatic, oxy, sulfur-containing or basic amino acid, or acidic amino acid amide.

It is well known in the art that the aliphatic amino acid includes glycine, alanine, valine, leucine and isoleucine; the oxy amino acid includes serine and threonine; the sulfur-containing amino acid includes cysteine, cystine and methionine; the aromatic amino acid includes phenylalanine, tyrosine and tryptophan; the imino acid includes proline; the acid amino acid amide includes asparagine and glutamine; the acidic amino acid includes asparagic acid and glutamic acid; the basic amino acid includes lysine, arginine and histidine.

As a typical example of the substitution of the amino acid residue described above, there can be exemplified an amino acid substitution selected from the group consisting of: A298I, A298V, V338M, S340G, S340N, S340V, S340W, H341A, H341C, H341D, H341E, H341F, H341G, H341I, H341K, H341L, H341M, H341N, H341P, H341Q, H341R, H341S, H341V, H341W, H341Y, D343A, D343E, D343F, D343H, D343I, D343K, D343L, D343M, D343N, D343Q, D343R, D343S, D343W, D343Y, D343V, G352A, G352C, G352D, G352E, G352F, G352I, G352K, G352L, G352M, G352N, G352P, G352Q, G352R, G352S, G352T, G352V, G352W, G352Y, K354A, K354C, K354D, K354E, K354F, K354G, K354H, K354M, K354N, K354P, K354Q, K354Y, K354R, K354S, Y424C, Y424D, Y424E, Y424K, Y424N, Y424Q, Y424R, Y424S, Y424T, Y424V, G426A, G426C, G426D, G426E, G426F, G426H, G426I, G426K, G426L, G426M, G426N, G426P, G426R, G426S, G426T, G426W, G426Y, G426V, V431F, F432I, F432K, F432L, F432M, F432Q, F432R, F432T and F432V, and any combination thereof.

The susceptibility defined in the present specification is evaluated in terms of a relative activity that is determined in a system wherein the inhibitor coexists or not. The relative activity is derived from a relative value (%) of an enzymatic activity (a sample value) obtained with the addition of the inhibitor in the determination of the enzymatic activity described in the present specification as compared with an enzymatic activity (a blank value) as "100%" obtained without the addition of the inhibitor in the same determination. Thus, the higher the relative activity is, the less the susceptibility to the inhibitor is (or the more the susceptibility to the inhibitor is reduced), vice versa.

It is desired that the modified GLD according to the present invention has at least 40%, preferably at least 60%, more preferably at least 80%, much more preferably at least 90%, most preferably at least 95% of the relative activity when determined in the system wherein the inhibitor coexists at a final concentration of 1 mM as compared with the enzymatic activity determined in the system wherein the inhibitor does not coexist. As the susceptibility may fluctuate depending on the culture conditions of the transformants and determination of the enzymatic activity, the enzymatic activity has to be determined in the same conditions.

The "inhibitor" in the present specification means any compound that is capable of inhibiting the wild-type FAD-conjugated glucose dehydrogenase (GLD) represented by SEQ ID NO: 1. For example, 1,10-phenanthroline and proflavin hydrochloride, and any compound having the chemical structure or physicochemical properties similar to them and capable of substantially inhibiting the wild-type GLD.

Accordingly, preferable examples of the modified GLD of the present invention include those comprising the amino acid sequence of a wild-type FAD-conjugated glucose dehydrogenase (GLD) represented by SEQ ID NO: 1 having a substitution of at least one amino acid residue selected from the group consisting of:
H341D, H341G, H341L, H341S, D343M, G352E, G352Q, G352Y, G426I, G426K, G426L, G426V, F432L, F432I, F432K and F432R, which has 90%-95% of the relative activity when determined in the system wherein the inhibitor coexists at the final concentration of 1 mM as compared with the enzymatic activity determined in the system wherein the inhibitor does not coexist; and S340W, H341A, H341C, H341F, H341I, H341K, H341M, H341Q, H341V, H341W, D343F, D343K, D343L, D343V and D343Y, which has more than 95% of the relative activity when determined in the system wherein the inhibitor coexists at the final concentration of 1 mM as compared with the enzymatic activity determined in the system wherein the inhibitor does not coexist.

The above substitution of the amino acids may be also made in an amino acid sequence having at least 60%; more preferably at least 70%, at least 80%, at least 85%, at least 90% and at least 95%; and most preferably at least 98% of identity with that of the wild-type FAD-conjugated glucose dehydrogenase (GLD) represented by SEQ ID NO: 1 or in terms of the amino acid position (at the corresponding position) of the wild-type GLD. The "identity" means one obtained in comparison of the whole sequence of a subject sequence with that of a standard sequence. The percentage of such identity may be calculated with any known or commercially available software that compares the standard sequence as a reference one. For example, BLAST, FASTA or GENETYX (Software Developing Corporation) may be used with their default parameters.

The modified GLD of the invention may further have the substitution, deletion or addition of one to several amino acid residues (for example, 1-5 amino acids, preferably 1-3 amino acid residues) in the amino acid sequence represented by SEQ ID NO: 1 in addition to the above substitutions of the amino acids, as long as it has the reduced susceptibility to the inhibitors, as compared with the wild-type GLD.

As one example of the polynucleotide encoding the modified GLD of the invention, a polynucleotide having a base sequence represented by SEQ ID NO: 2 which is a polynucleotide encoding the amino acid sequence of the wild-type GLD represented by SEQ ID NO: 1 can be exemplified. Other than this, a different codon may be used as long as the codon encodes the same amino acid residue. For example, a usage codon can be appropriately optimized depending on the kind of a host cell to be transformed with the polynucleotide or the like.

Incidentally, in the invention, the "polynucleotide" refers to a molecule in which 100 or more phosphate esters of nucleosides in which a purine or a pyrimidine is attached to a sugar via a β-N-glycosidic bond (ATP (adenosine triphosphate), GTP (guanosine triphosphate), CTP (cytidine triphosphate) or UTP (uridine triphosphate); or dATP (deoxyadenosine triphosphate), dGTP (deoxyguanosine triphosphate), dCTP (deoxycytidine triphosphate) or dTTP (deoxythymidine triphosphate). Specific examples thereof include a chromosomal DNA (a DNA containing an intron) encoding the modified GLD of the invention, a mRNA transcribed from the chromosomal DNA, a cDNA synthesized from the mRNA, and a polynucleotide amplified by PCR using any of these as a template. An "oligonucleotide" refers to a molecule in which 2 to 99 nucleotides are linked to one another. Further, the "polypeptide" refers to a molecule formed from 30 or more amino acid residues which are linked to one another via an amide bond (peptide bond) or an unnatural residual linkage, and also those with the addition of a sugar chain, those subjected to artificial chemical modification, and the like are included. Further, in the polynucleotide of the invention, also a base sequence encoding a signal sequence of the modified GLD can be appropriately included depending on the kind of a transformed cell or the like.

The polynucleotide of the invention can be easily prepared by an arbitrary method known to those skilled in the art. For example, as specifically described in Examples of this description, a wild-type GLD gene is isolated from a plasmid containing a polynucleotide having a base sequence represented by SEQ ID NO: 2, and introducing a random mutation or a site-specific mutation by utilizing any of various PCR methods known to those skilled in the art using an appropriate oligonucleotide primer (probe) set based on the isolated gene, whereby the polynucleotide encoding the modified GLD of the invention can be prepared.

Further, the polynucleotide of the invention can be synthesized in vitro by a well-known chemical synthesis technique as described in a document (such as Carruthers (1982) Cold Spring Harbor Symp. Quant. Biol. 47: 411-418; Adams (1983) J. Am. Chem. Soc. 105: 661; Belousov (1997) Nucleic Acid Res. 25: 3440-3444; Frenkel (1995) Free Radic. Biol. Med. 19: 373-380; Blommers (1994) Biochemistry 33: 7886-7896; Narang (1979) Meth. Enzymol. 68: 90; Brown (1979) Meth. Enzymol. 68: 109; Beaucage (1981) Tetra. Lett. 22: 1859; or U.S. Pat. No. 4,458,066).

The recombinant vector of the invention can be prepared by an arbitrary method known to those skilled in the art using an appropriate cloning vector or expression vector depending on the kind of a polynucleotide to be used as an insert, an intended use thereof, or the like. For example, in the case where the modified GLD of the invention is produced using a cDNA or an ORF region thereof as an insert, an expression vector for in vitro transcription, or also an expression vector suitable for the respective prokaryotic cells such as *Escherichia coli* and *Bacillus subtilis*; and eukaryotic cells such as yeasts, filamentous fungi (such as molds), insect cells, and mammalian cells can be used.

As the transformed cell of the invention, for example, a prokaryotic cell such as *Escherichia coli* or *Bacillus subtilis*; a eukaryotic cell such as a yeast, a mold such as *Aspergillus oryzae*, an insect cell or a mammalian cell; or the like can be used. As for such a cell, a host can be suitably selected in accordance with the need of a sugar chain or other peptide modification for the modified GLD. Such a transformed cell can be prepared by introducing a recombinant vector into a cell by an arbitrary method known to those skilled in the art such as an electroporation method, a calcium phosphate method, a liposome method or a DEAE dextran method. Specific examples of the recombinant vector and the transformed cell include a recombinant vector shown in the below-mentioned Examples and a transformed *Escherichia coli* and a transformed mold prepared with this vector.

In the case where the modified GLD of the invention is produced by expressing a DNA in a microorganism such as *Escherichia coli*, a recombinant expression vector in which the above-mentioned polynucleotide has been introduced into an expression vector having an origin, a promoter, a ribosome-binding site, a DNA cloning site, a terminator sequence, and the like and replicable in the microorganism is prepared, a host cell is transformed with this expression vector, and the resulting transformant is cultured, whereby the modified GLD can be produced in a large amount in the microorganism. At this time, if a start codon and a stop codon are introduced upstream and downstream of an arbitrary coding region and the DNA is expressed, a modified GLD fragment containing the arbitrary region can also be obtained. Alternatively, the enzyme can also be expressed as a fusion protein with another protein. By cleaving this fusion protein with an appropriate protease, the target modified GLD can also be obtained. Examples of the expression vector for *Escherichia coli* include a pUC system, pBluescript II, a pET expression system, a pGEX expression system, and a pCold expression system.

Alternatively, in the case where the modified GLD of the invention is produced by expressing it in a eukaryotic cell, a recombinant vector is prepared by inserting the above-mentioned polynucleotide into an expression vector for a eukaryotic cell having a promoter, a splicing region, a poly(A) addition site, and the like, and the resulting recombinant vector is introduced into a eukaryotic cell, whereby the modified GLD can be produced in the eukaryotic cell. The polynucleotide can be maintained in a cell in a state of a plasmid or the like, or can be maintained by incorporating the polynucleotide into a chromosome. Examples of the expression vector include pKA1, pCDM8, pSVK3, pSVL, pBK-CMV, pBK-RSV, an EBV vector, pRS, and pYE82. Further, if pIND/V5-His, pFLAG-CMV-2, pEGFP-N1, pEGFP-C1 or the like is used as the expression vector, an FAD-conjugated glucose dehydrogenase polypeptide can also be expressed as a fusion protein to which any of a variety of tags such as a His tag, a FLAG tag or GFP has been attached. As the eukaryotic cell, a cultured mammalian cell such as a monkey kidney cell COS-7 or a Chinese hamster ovary cell CHO; a budding yeast, a fission yeast, a mold, a silkworm cell or a *Xenopus* oocyte is generally used. Any kind of the above eukaryotic cells may be used as long as it can express the modified GLD of the invention. In order to introduce the expression vector into the eukaryotic cell, a known method such as an electroporation method, a calcium phosphate method, a liposome method or a DEAE dextran method can be used.

In particular, it is preferred to perform cloning wherein an appropriate *Aspergillus oryzae* strain is transformed with a recombinant vector derived from *Aspergillus oryzae* containing a polynucleotide encoding the modified GLD of the invention.

In order to collect, in other words, isolate and purify the target protein from a culture (such as microbial cells or a culture broth or a culture medium composition containing the enzyme secreted to the outside of microbial cells) after the modified GLD of the invention is expressed in a prokaryotic cell or a eukaryotic cell, known separation procedures can be combined. Examples of such procedures include a treatment with a denaturant such as urea or a surfactant, a heat treatment, a pH treatment, an ultrasonication treatment, enzymatic digestion, salting out, a solvent sedimentation method, dialysis, centrifugal separation, ultrafiltration, gel filtration, SDS-PAGE, isoelectric focusing, ion exchange chromatography, hydrophobic chromatography, reverse-phase chromatography, and affinity chromatography (also including a method utilizing a tag sequence, and a method using a polyclonal antibody or a monoclonal antibody specific for the modified GLD). By using such a method, the modified GLD of the invention can be produced in a large amount.

Further, the modified GLD of the invention can be produced in vitro by preparing an RNA through in vitro transcription from a vector containing the polynucleotide (a cDNA or its coding region thereof) of the invention and performing in vitro translation using the RNA as a template.

In the case where the modified GLD is produced by in vitro expression, the above-mentioned polynucleotide is inserted into a vector having a promoter to which an RNA polymerase can bind thereby preparing a recombinant vector. This vector is then added to an in vitro translation system such as a rabbit reticulocyte lysate or a wheat germ extract including the RNA polymerase corresponding to the promoter, whereby the modified GLD can be produced in vitro. Examples of the promoter to which the RNA polymerase can bind include T3, T7, and SP6. Examples of the vector containing these promoters include pKA1, pCDM8, pT3/T718, pT7/319, and pBluescript II.

The modified GLD of the invention which can be produced by the method described above is an enzyme which catalyzes a reaction of the dehydrogenation of glucose in the presence of an electron acceptor, and therefore, the use thereof is not particularly limited as long as a change caused by this reaction can be utilized. For example, it can be used in the medical field or the clinical field such as the use in the determination of glucose in a sample containing a biological material, a reagent for use in the determination thereof, or a reagent for use in the elimination thereof, and also it can be used in the production of a substance using a coenzyme-conjugated glucose dehydrogenase.

The modified GLD of the present invention can be used as the reagent for the determination of glucose. The reagent may optionally contain any component known in the art such as a buffer and thermal stabilizer selected from the group consisting of bovine serum albumin (BSA), egg albumin, sugars or sugar alcohols that are not reactive with the enzyme, carboxyl-containing compounds, alkali earth metal compounds, ammonium salts, sulfates and proteins so as to increase thermal stability or storage stability. It may further contain any known compound that can suppress the effect by the existence of a contaminant to the determination.

The modified GLD of the present invention can be used in a biosensor as a glucose sensor that determines the glucose concentration in a liquid sample.

The biosensor of the invention uses a reaction layer containing the modified GLD of the invention as an enzyme. The biosensor is produced by, for example, forming an electrode system comprising a working electrode, its counter electrode, and a reference electrode on an insulating base plate using a method such as screen printing or vapor deposition, and providing a determination reagent comprising an oxidoreductase and an electron acceptor. When a sample liquid containing a substrate is contacted with the determination reagent, the enzyme will dissolve and react with the substrate so as to reduce the electron acceptor. After completion of the enzymatic reaction, the reduced electron acceptor is electrochemically oxidized. At this time, this biosensor can determine the substrate concentration in the sample liquid from the oxidation current value obtained. In addition, other than this, a biosensor of a type that detects a coloring intensity, a pH change, or the like can also be constructed. By selecting an enzyme that catalyzes a substance as its substrate to be determined, any substance can be determined.

As the electron acceptor of the biosensor, a chemical substance having an excellent ability to donate and accept electrons can be used. The chemical substance having such excellent ability is a chemical substance or proteinous electron mediator, which is generally called "an electron carrier", "a mediator" or "a redox mediator". An electron carrier or a redox mediator cited in, for example, JP-T-2002-526759 or the like may be used as said chemical substance.

The modified GLD according to the present invention may be used in a bio-battery. A bio-battery of the present invention is constituted with an anode pole that performs an oxidation reaction and a cathode pole that performs a reduction reaction, which may include an electrolyte separating the anode from the cathode, if necessary. Using an enzyme electrode including the above electron mediator and glucose oxidoreductase or the above fusion body for the anode electrode, an electron generated by oxidizing the substrate is taken out to the electrode and a proton is simultaneously generated. At the same time, for the cathode side, an enzyme commonly used for a cathode electrode may be used, and using laccase, ascorbate oxidase or bilirubin oxidase, for example, water is generated by a reaction of the proton generated on the anode side with oxygen. For the electrode, an electrode commonly used for a bio-battery such as carbon, gold, and platinum may be used.

[Method for Determination of Enzymatic Activity]

1.0 mL of 0.1 M potassium phosphate buffer (pH 7.0), 1.0 mL of 1.0 M D-glucose, 0.14 mL of 3 mM 2,6-dichlorophenol indophenol (hereinafter referred to as DCIP), 0.2 mL of 3 mM 1-methoxy-5-methylphenazinium methylsulfate (hereinafter referred to as 1-m-PMS), 0.06 mL of methanol and 0.55 mL of distilled water are added to a 3-mL quartz cell (light path length: 1 cm), and the cell is placed in a spectrophotometer provided with a thermostat cell holder and incubated at 37° C. for 10 minutes. Thereafter, 0.05 mL of an enzyme solution is added to the cell, and then, a change in the absorbance of DCIP at 600 nm (ΔABS/min) is determined. The molar extinction coefficient of DCIP at pH 7.0 is taken as $16.3 \times 10^3$ $cm^{-1} M^{-1}$, and enzymatic activity to reduce 1 μmol of DCIP per minute is substantially equivalent to 1 unit of the enzymatic activity. Therefore, the enzymatic activity is determined from the change in the absorbance according to Equation I. In Example 8, methanol was replaced with the same amount of distilled water.

The enzymatic activity is determined in the following manner in Examples 3 and 6 wherein a plate reader (Japan Molecular Device Corporation, SpectraMax Plus384) is used. Thus, culture supernatant that had been diluted in advance with an appropriate magnification is added to a 96-well microplate with an amount of 100 μl per well. A reagent for the determination of the enzymatic activity comprising phosphate buffer (pH 7.0), 1.0 M D-glucose, 3 mM DCIP, 3 mM 1-m-PMS and methanol with a volume ratio of 0.1:1:0.14:0.2:0.06 is added to the 96-well microplate with an amount of 100 μl per well, and a change in the absorbance of DCIP at 600 nm (ΔABS/min) is then determined. The enzymatic activity can be calculated by conversion in proportion to a change in the absorbance of an enzyme solution for which the enzymatic activity has already been known by the above-mentioned activity determination procedure using the spectrophotometer.

In the following examples, a value of the enzymatic activity determined by the spectrometer or plate reader using the above reagent composition is considered as a blank value. On the other hand, a sample value is determined using a methanol solution comprising the inhibitor such as 1,10-phenanthroline or proflavin hydrochloride at a final concentration of 1 mM instead of the methanol.

Enzymatic activity (unit/mL)=(−ΔABS/16.3)×3.0/ 0.05×(Dilution ratio of enzyme) [Equation 1]

Incidentally, various techniques used for implementing the invention can be easily and surely carried out by those skilled in the art based on publicly known documents and the like exclusive of techniques the sources of which are indicated specifically. For example, the genetic engineering and molecular biological techniques can be carried out based on the methods described in Sambrook and Maniatis, in Molecular Cloning: A Laboratory Manual, Cold Spring Harbor Laboratory Press, New York, 1989; Ausubel, F. M. et al., Current Protocols in Molecular Biology, John Wiley & Sons, New York, N.Y., 1995; and the like or the methods described in the references cited therein or methods substantially equivalent thereto or modified methods thereof. In addition, the terms in the invention are basically in accordance with IUPAC-IUB Commission on Biochemical Nomenclature or the meanings of terms conventionally used in the art.

Hereinafter, the invention will be more specifically described with reference to Examples. However, the technical scope of the invention is by no means limited to the description thereof. Further, the contents described in the documents cited in this description constitute the disclosure of this description as a part thereof.

EXAMPLE 1

Construction of Plasmid pAFF4

A GLD gene derived from *Aspergillus terreus* FERM BP-08578 strain disclosed in Patent document 1 was isolated by a common procedure, followed by removal of a polynucleotide encoding a signal sequence (amino acids at position 1-19 in the SEQ ID NO:1) from said gene to obtain a wild-type GLD gene. The PCR was then performed by using the wild-type GLD gene as a template and oligonucleotides represented by SEQ ID NO: 3 and NO:4 as a primer DNA (F) and a primer DNA (R), respectively. The primer DNA (F) had been phosphorylated in advance. The resulting PCR product was treated with SalI and introduced into a plasmid pAFF2 (given over by National Institute of Advanced Industrial Science and Technology at 3-1, Kasumigaseki 1-chome, Chiyoda-ku, Tokyo 100-8921 JAPAN) that had been treated with NaeI and SalI and dephosphorylated at the NaeI cleavage site to obtain a plasmid pAFF3GLD. Next, the PCR was then performed by using the wild-type GLD gene as a template and oligonucleotides represented by SEQ ID NO: 5 and NO:6 as a primer DNA (F) and a primer DNA (R), respectively. The resulting PCR product was treated with BglII and SphI, and introduced into the plasmid pAFF3GLD that had been treated with BglII and SphI to obtain a plasmid pAFF4GLD.

```
Primer DNA(F):                           (SEQ ID NO: 3)
5' ggcagatcttccaactccacgtccgccaaatatgattat 3'

Primer DNA(R):                           (SEQ ID NO: 4)
5' ctgcaggtcgacgcatgcctaacgacgaccagcatcggccttga tgag 3'

Primer DNA (F):                          (SEQ ID NO: 5)
5' ggcagatcttccaactccacgtccgccaaatatgattat 3'

Primer DNA (R):                          (SQ ID NO: 6)
5' acatgcatgctctagactaacgacgaccagcatcggccttgatg ag 3'
```

EXAMPLE 2

Acquisition of Transformant Having Modified GLD Gene Having Random Mutation Introduced Therein In order to introduce a random mutation into the wild-type GLD gene, oligonucleotides as shown below were designed and synthesized. A primer DNA (F) has a restriction enzyme BglII cleavage site, and a primer DNA (R) has a restriction enzyme XbaI cleavage site.

```
Primer DNA (F):                      (SEQ ID NO: 7)
5'ggcagatcttccaactccacgtccgccaaatatgattat 3'

Primer DNA (R):                      (SEQ ID NO: 8)
5'acatgcatgctctagactaacgacgaccagcatcggccttgatgag
3'
```

Using the plasmid pAFF4GLD containing the wild-type GLD gene (SEQ ID NO: 2) obtained in Example 1, and the primer DNA (F) represented by SEQ ID NO: 7 and the primer DNA (R) represented by SEQ ID NO: 8 synthesized in Example 2, a plasmid into which a random mutation was introduced was obtained by means of a GeneMorph II Random Mutagenesis Kit (manufactured by Stratagene, Inc.) according to an experimental procedure attached to the kit. After *E. coli* JM109 Competent Cells (manufactured by Takara Bio Inc.) used as a host were subjected to transformation, the resulting cells were plated on an LB agar plate containing ampicillin sodium (manufactured by Wako Pure Chemical Industries, Ltd.) serving as a selection marker at a concentration of 50 μg/mL and cultured overnight at 37° C., whereby transformants were obtained. The plasmid having the random mutation introduced therein was then extracted from the resulting *E. coli* transformant using illustra plasmid mini spin kit (GE Health Care Inc.). The extracted plasmid was then introduced into *Saccharomyces cerevisiae* BY4741 (for example, Product No. YSC1048 of OpenBiosystems Inc.) by means of Frozen-EZ Yeast Transformation II Kit (ZYMO RESEARCH INC.).

EXAMPLE 3

Evaluation of Enzymatic Activity of GLD in Transformant Having the Modified GLD Gene Having Random Mutation Introduced Therein Into each well of a 96-well microplate (manufactured by Nunc, Inc.), a YPD medium containing 125 μL of 1.0% (w/v) yeast extract (manufactured by BD), 2.0% (w/v) tryptone (manufactured by BD), 2.0% (w/v) glucose (manufactured by Wako Pure Chemical Industries, Ltd.) was dispensed, and the transformant colonies obtained in Example 2 were inoculated thereinto one by one.

After shaking culture at 30° C. and 1,000 rpm for 24 hours, the culture mixture was centrifuged and the supernatant was collected.

According to the above-mentioned method for the determination of enzymatic activity, a blank value and a sample value were determined using a plate reader, and the relative activity (%) was obtained by dividing the sample value by the blank value. The mutant strains that showed a significant increase in the relative activity were selected and isolated, and subjected to a gene analysis to give the results shown in Table 1.

TABLE 1

| Mutant | Relative Activity |
| --- | --- |
| S272T + A298V + A369T | 68.6 |
| V338 + Q382H | 60.0 |
| L250V + S340G + D399N | 43.4 |
| H341L | 69.7 |

TABLE 1-continued

| Mutant | Relative Activity |
| --- | --- |
| H341R + G499S | 71.9 |
| D343N + S490C | 71.1 |
| R250L + V323A + D343E | 54.3 |
| N287D + D343E + K494E | 52.2 |
| D343N | 65.2 |
| D343E + L562H | 51.8 |
| D343N + S490C | 61.8 |
| G352E | 70.4 |
| M342L + K354N | 69.8 |
| G426S + A578V | 65.7 |
| V431M | 44.8 |
| F432L | 80.4 |
| Wild-type | 25.7 |

EXAMPLE 4

Acquisition of Transformant Having Modified GLD Gene Having Site-Specific Substitution Mutation Introduced Therein Part 1

In order to introduce a site-specific substitution mutation into the GLD gene, oligonucleotides as shown below were designed and synthesized.

In the following oligonucleotides, a codon "nnn" means any nucleotide sequence encoding an amino acid of the substitution mutation. For example, the following nucleotide sequences (codons) mean each amino acid of the substitution mutation:

"gcc" for alanine (A), "tgc" for cysteine (C), "gac" for aspargic acid (D), "gag" for gultamic acid (E), "ttc" for phenylalanine (F), "ggc" for glycine (G), "cac" for histidine (H), "atc" for isoleucine (I), "aag" for lysine (K), "ctt" for leucine (L), "atg" for methionine (M), "aac" for asparagine (N), "ccc" for proline (P), "cag" for glutamine (Q), "cgt" for arginine (K), "tcc" for serine (S), "act" for threonine (T), "gtc" for valine (V), "tgg" for tryptophan (W), and "tat" for tyrosine (Y). These nucleotides were selected in accordance with the sequence represented by SEQ ID NO:2.

A primer that was used for the substitution mutation of alanine (A) at position 298 with any amino acid is represented by SEQ ID NO:9. Primers used for the substitution mutation at the different positions are also shown below:

```
Primer DNA (A298):             (Sequence ID NO: 9)
5' tgtctctgccggtnnnttgaagtccccggc 3'

Prime DNA (S340):              (Sequence ID NO: 10)
5' aggaccaagtgaacnnncacatggatgcat 3'

Primer DNA (H341):             (Sequence ID NO: 11)
5' ccaagtgaacagcnnnatggatgcatcggg 3'

Primer DNA (D343):             (Sequence ID NO: 12)
5' gaacagccacatgnnngcatcgggcaacac 3'

Primer DNA (G352):             (Sequence ID NO: 13)
5' cacttccatctctnnnaccaaggcagtctc 3'

Primer DNA (K354):             (Sequence ID NO: 14)
5' catctctggaaccnnngcagtctcctaccc 3'

Primer DNA (Y424):             (Sequence ID NO: 15)
5' tgaagtcctgaacnnnccgggcagcgcgac 3'
```

-continued

```
Primer DNA (V431):         (Sequence ID NO: 16)
5' cagcgcgacgtccnnntttgcagaattctg 3'

Primer DNA (F432):         (Sequence ID NO: 17)
5' cgcgacgtccgtgnnngcagaattctgggc 3'
```

EXAMPLE 5

Using the plasmid pAFF4GLD containing the wild-type GLD gene obtained in Example 1, the primer DNA represented by SEQ ID NO: 9 synthesized in Example 4, and a synthetic oligonucleotide complementary to said primer DNA a, a plasmid into which a substitution mutation was introduced was obtained by means of a QuikChange II Site-Directed Mutagenesis Kit (manufactured by Stratagene, Inc.) according to an experimental procedure attached to the kit. After *E. coli* JM109 Competent Cells (manufactured by Takara Bio Inc.) used as a host was subjected to transformation, the resulting cells were plated on the LB agar (manufactured by BD) plate containing ampicillin sodium (manufactured by Wako Pure Chemical Industries, Ltd.) serving as a selection marker at 50 μg/mL and cultured overnight at 37° C., whereby a transformant having a modified GLD gene encoding a modified GLD having the substitution of alanine at position 298 of the amino acid sequence of the wild-type GLD with each amino acid was obtained.

In the same manner as the above-mentioned method, a plasmid into which each substitution mutation was introduced was obtained using the plasmid pAFF4GLD containing the wild-type GLD gene, each of the primer DNAs represented by SEQ ID NOS: 10 to 17 synthesized in Example 4, and a synthetic oligonucleotide complementary to each of the primer DNAs. Transformation was also performed in the same manner as described above, and a transformant having a modified GLD gene encoding each modified GLD with the substitution of each amino acid sequence of the wild-type GLD was obtained.

Furthermore, in the same manner as Example 2, the plasmid having the site-specific substitution mutation introduced was then extracted from the resulting *E. coli* transformants using illustra plasmid mini spin kit (GE Health Care Inc.). The extracted plasmid was then introduced into *Saccharomyces cerevisiae* BY4741.

EXAMPLE 6

Evaluation of Enzymatic Activity of GLD in Transformant Having Modified GLD Gene Having the Site-Specific Substitution Mutation Introduced Therein Part 1

In the same manner as the procedure described in Example 3, the mutant strains that showed a significant increase in the relative activity were selected with respect to the yeast transformants obtained in Example 5. The results of the relative activity of the thus selected mutant strains are shown in Tables 2-4.

The susceptibility was also significantly reduced not only to 1,10-phenanthroline but also to proflavin hydrochloride (45% or more of the relative activity for the inhibition by proflavin hydrochloride) with respect to the mutant having the following mutation:
A298V, V338M, S340G, S340N, S340V, S340W, H341A, H341C, H341D, H341F, H341G, H341I, H341K, H341L, H341M, H341N, H341Q, H341R, H341S, H341V, H341W, H341Y, D343A, D343E, D343F, D343H, D343I, D343K, D343L, D343M, D343N, D343Q, D343S, D343W, D343Y, D343V, G352A, G352F, G352I, G352M, G352N, G352P, G352Q, G352R, G352S, G352W, G352Y, Y424C, Y424K, Y424N, Y424Q, Y424R, Y424S, Y424V, G426A, G426C, G426F, G426H, G426I, G426K, G426L, G426M, G426N, G426S, G426T, G426W, G426Y, G426V, V431F, F432I, F432K, F432L, F432M, F432Q, F432R, F432T and F432V.

TABLE 2

| | Relative Activity [%] | |
|---|---|---|
| | 1,10-Phenanthroline | Proflavin hydrochloride |
| Wild-type | 30.0 | 35.0 |
| A298I | 73.7 | 43.8 |
| A298V | 62.2 | 51.2 |
| V338M | 73.6 | 55.0 |
| S340G | 54.6 | 49.5 |
| S340N | 82.0 | 49.9 |
| S340V | 84.2 | 54.9 |
| S340W | 97.7 | 75.7 |
| H341A | 95.1 | 75.8 |
| H341C | 95.4 | 67.7 |
| H341D | 90.0 | 64.5 |
| H341E | 88.4 | 25.2 |
| H341F | 97.1 | 67.5 |
| H341G | 93.8 | 76.9 |
| H341I | 97.4 | 64.4 |
| H341K | 99.2 | 61.3 |
| H341L | 92.2 | 66.9 |
| H341M | 95.4 | 71.4 |
| H341N | 93.3 | 81.5 |
| H341P | 88.3 | 43.2 |
| H341Q | 97.5 | 68.1 |
| H341R | 78.6 | 69.5 |
| H341S | 90.4 | 76.6 |
| H341V | 96.1 | 71.4 |
| H341W | 100.3 | 88.4 |
| H341Y | 93.6 | 77.8 |
| D343A | 72.5 | 51.2 |
| D343E | 61.4 | 58.2 |
| D343F | 95.3 | 65.7 |
| D343H | 87.5 | 62.8 |
| D343I | 88.6 | 71.5 |
| D343K | 95.9 | 51.8 |
| D343L | 100.5 | 73.2 |
| D343M | 91.2 | 52.9 |
| D343Q | 86.2 | 47.0 |
| D343R | 80.7 | 37.9 |
| D343S | 70.1 | 48.3 |
| D343V | 96.7 | 67.7 |
| D343W | 94.2 | 57.9 |
| D343Y | 96.2 | 55.6 |

TABLE 3

| | Relative Activity [%] | |
|---|---|---|
| | 1,10-Phenanthroline | Proflavin hydrochloride |
| Wild-type | 30.0 | 35.0 |
| G352A | 76.1 | 47.9 |
| G352C | 86.2 | 43.8 |
| G352D | 87.8 | 42.7 |
| G352E | 91.7 | 36.3 |
| G352F | 83.8 | 56.9 |
| G352I | 85.5 | 60.9 |
| G352K | 82.5 | 32.7 |
| G352L | 80.7 | 43.7 |
| G352M | 74.7 | 45.7 |
| G352N | 80.5 | 55.8 |
| G352P | 89.8 | 49.1 |
| G352Q | 90.4 | 56.4 |

TABLE 3-continued

| | Relative Activity [%] | |
|---|---|---|
| | 1,10-Phenanthroline | Proflavin hydrochloride |
| G352R | 80.3 | 68.1 |
| G352S | 62.9 | 38.7 |
| G352T | 85.4 | 44.1 |
| G352V | 87.0 | 41.6 |
| G352W | 81.2 | 48.1 |
| G352Y | 92.4 | 52.8 |
| K354A | 66.2 | 8.9 |
| K354C | 62.6 | 14.4 |
| K354D | 70.8 | 11.6 |
| K354E | 60.0 | 20.7 |
| K354F | 47.8 | 16.0 |
| K354G | 60.8 | 23.0 |
| K354H | 52.6 | 11.1 |
| K354M | 53.5 | 10.7 |
| K354N | 61.9 | 15.1 |
| K354P | 64.3 | 16.7 |
| K354Q | 71.4 | 12.5 |
| K354Y | 56.0 | 15.1 |
| K354H | 51.0 | 11.6 |
| K354R | 64.4 | 12.6 |
| K354S | 71.6 | 21.3 |
| Y424C | 73.7 | 45.9 |
| Y424D | 87.1 | 37.2 |
| Y424E | 87.5 | 37.1 |
| Y424K | 71.9 | 52.5 |
| Y424N | 89.9 | 55.6 |
| Y424Q | 80.2 | 50.2 |
| Y424R | 70.3 | 55.6 |
| Y424S | 81.4 | 61.0 |
| Y424T | 71.2 | 43.4 |
| Y424V | 49.1 | 46.7 |

TABLE 4

| | Relative Activity [%] | |
|---|---|---|
| | 1,10-Phenanthroline | Proflavin hydrochloride |
| Wild-type | 30.0 | 35.0 |
| G426A | 68.7 | 51.2 |
| G426C | 78.0 | 64.1 |
| G426D | 56.5 | 34.2 |
| G426E | 64.4 | 32.6 |
| G426F | 60.5 | 51.8 |
| G426H | 54.9 | 48.7 |
| G426I | 93.2 | 63.4 |
| G426K | 94.3 | 65.4 |
| G426L | 91.2 | 63.7 |
| G426M | 78.3 | 58.8 |
| G426N | 69.6 | 51.9 |
| G426P | 56.1 | 33.3 |
| G426R | 71.5 | 43.0 |
| G426S | 80.9 | 58.0 |
| G426T | 88.5 | 58.4 |
| G426W | 61.0 | 47.8 |
| G426Y | 61.6 | 47.5 |
| G426V | 90.3 | 59.9 |
| V431F | 82.1 | 57.7 |
| F432T | 89.9 | 80.2 |
| F432V | 80.2 | 70.3 |
| F432L | 91.7 | 68.1 |
| F432I | 91.8 | 80.9 |
| F432K | 92.1 | 79.3 |
| F432M | 62.5 | 71.1 |
| F432M | 74.2 | 66.1 |
| F432Q | 59.3 | 67.3 |
| F432R | 86.2 | 73.7 |
| F432R | 94.2 | 72.6 |

EXAMPLE 7

Evaluation of the Susceptibility to 1,10-Phenanthroline and Proflavin Hydrochloride Using a Purified Enzyme The mutants having the mutation of H341W and F432L, respectively, were inoculated into a shake flask containing 150 mL the YPD medium. After shaking culture at 30° C. and 120 rpm for 48 hours, the culture mixture was centrifuged at 3,000×g for 5 min. and the supernatant was filtered through a membrane filter with 10 μm.

The resulting filtrate was concentrated using Viva spin 20-10 k (GE Health Care Inc.) and desalted until its electro conductivity had been dropped to 10 μS/cm or less.

The resulting enzyme solution was passed through a DEAE Cellufine A-500-m column (1.0 cm in diameter×6.0 cm in height) equilibrated with 1 mM potassium phosphate buffer (pH 7.0). After the column was washed with the same buffer, 10 mM potassium phosphate buffer (pH 7.0) was passed through the column. The resulting active fractions were collected and concentrated with Viva spin 20-10 k (GE Health Care Inc.) to obtain a purified enzyme.

After diluting the purified enzyme to an appropriate concentration, the sample value and blank value were determined in accordance with the method for determination of the enzymatic activity using the spectrophotometer. The results in Table 5 show that the susceptibility was much reduced both to 1,10-Phenanthroline and to proflavin hydrochloride.

TABLE 5

| Modified GLD | Relative Activity [%] 1,10-Phenanthroline | Relative Activity [%] proflavin hydrochloride |
|---|---|---|
| H341W | 89.5 | 144.3 |
| F432L | 90.8 | 88.1 |
| Wild-type GLD | 41.1 | 50.9 |

EXAMPLE 8

Evaluation of the Susceptibility to the Inhibitors at a High Concentration

The relative activity was determined in the same manner as in Examples 3 and 6 in the co-existence of the inhibitors at a high concentration. The results in Table 6 show that the relative activity of the modified GLD of the present invention was significantly increased as compared with that of the wild-type GLD in the presence of the inhibitors at a final concentration of 1-20 mM.

TABLE 6

| | Final Conc.[mM] | Relative Activity[%] F432L | Relative Activity[%] H341W |
|---|---|---|---|
| 1,10-phenanthroline | 1 | 97.0 | 99.4 |
| | 5 | 64.2 | 78.1 |
| | 10 | 47.2 | 63.2 |
| | 20 | 32.1 | 45.8 |
| Proflavin | 2 | 91.6 | 138.2 |

EXAMPLE 9

Quantitative Determination of D-Glucose Using the Modified GLD

Figure 1B:
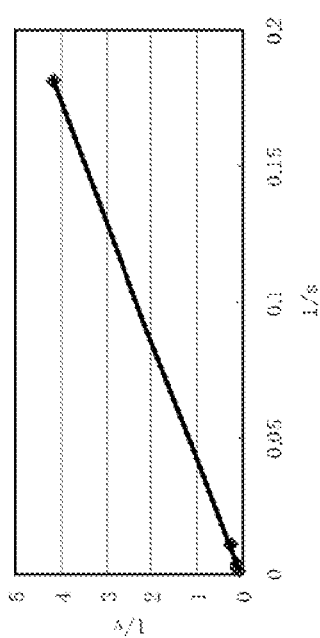
FIG. 1B shows a calibration curve for use in the determination of glucose obtained using a modified GLD "H341W" of the invention. X axis: 1/(Substrate concentration [mM]), Y axis: 1/(Reaction rate)
Figure 1C:
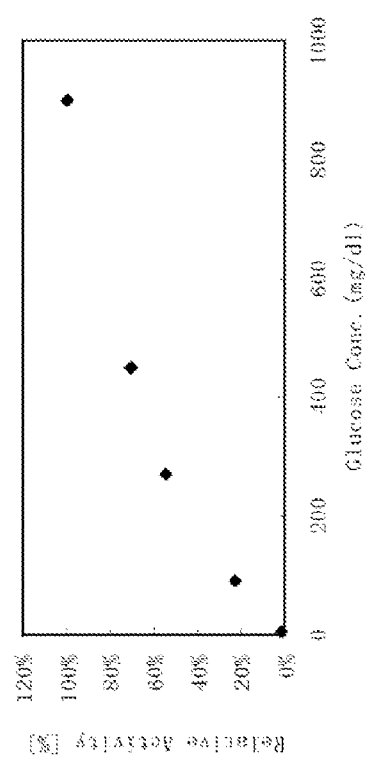
FIG. 1C shows a calibration curve for use in the determination of glucose obtained using a modified GLD "F432L" of the invention. X axis: Substrate concentration [mg/dL], Y axis: Relative activity [%]
Figure 1D:
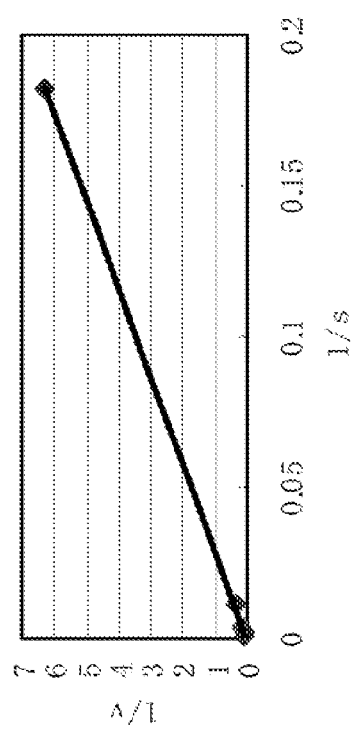
FIG. 1D shows a calibration curve for use in the determination of glucose obtained using a modified GLD "F432L" of the invention. X axis: 1/(Substrate concentration [mM]), Y axis: 1/(Reaction rate)

Quantitative determination of D-glucose was carried out in accordance with the above method for determination of enzymatic activity with the spectrophotometer using the modified GLD having the substitution of H431W and F432L, respectively. D-glucose was added to the determination system at a final concentration of 0.3, 5.0, 15, 25 and 50 mM, respectively, and a change in the absorbance of DCIP at 600 nm (ΔABS/min) was determined. The resulting change in the absorbance was then plotted against the above concentration of D-glucose to give a calibration curve, as shown in FIG. 1A-1D. These results have proved that it is possible to quantitatively determine glucose using the modified GLD of the present invention

INDUSTRIAL APPLICABILITY

As the modified GLD encoded by the polynucleotide of the invention is less susceptible to 1,10-phenanthroline, it can be utilized also in a self-monitoring of blood glucose (SMBG) device with higher accuracy, and largely contributes to self-care and self-treatment by patients with diabetes.

---

What is claimed is:

1. An isolated polypeptide having glucose dehydrogenase (GLD) activity, wherein the polypeptide comprises all of SEQ ID NO: 1 except for at least one substitution at a position selected from the group consisting of positions 298, 338, 340, 341, 343, 352, 354, 426, 431 and 432 of SEQ ID NO: 1, and wherein the polypeptide has reduced susceptibility to inhibition by 1,10-phenanthroline, as compared with the polypeptide of SEQ ID NO: 1.

2. A method for the determination of glucose concentration, comprising contacting the isolated polypeptide of claim 1 with a sample to catalyze the dehydrogenation of glucose in the presence of an electron acceptor, wherein a change caused by this reaction is used to determine the glucose concentration of the sample.

3. A reagent composition for determining glucose concentration comprising the isolated polypeptide of claim 1.

4. A biosensor for determining glucose concentration comprising the isolated polypeptide of claim 1.

5. The isolated polypeptide according to claim 1, wherein the at least one substitution is one or more selected from the group consisting of:
A298I, A298V, V338M, S340G, 340N, S340V, 340W, H341A, H341C, H341D, H341E, H341F, H341G, H341I, H341K, H341L, H341M, H341N, H341P, H341Q, H341R, H341S, H341V, H341W, H341Y, D343A, D343E, D343F, D343H, D343I, D343K, D343L, D343M, D343N, D343Q, D343R, D343S, D343W, D343Y, D343V, G352A, G352C, G352D, G352E, G352F, G352I, G352K, G352L, G352M, G352N, G352P, G352Q, G352R, G352S, G352T, G352V, G352W, G352Y, K354A, K354C, K354D, K354E, K354F, K354G, K354H, K354M, K354N, K354P, K354Q, K354Y, K354R, K354S, G426A, G426C, G426D, G426E, G426F, G426H, G426I, G426K, G426L, G426M, G426N, G426P, G426R, G426S, G426T, G426W, G426Y, G426V, V431F, F432I, F432K, F432L, F432M, F432Q, F432R, F432T and F432V.

6. An isolated polypeptide having glucose dehydrogenase (GLD) activity, wherein the polypeptide comprises all of SEQ ID NO: 1 except for at least one substitution at a position of SEQ ID NO: 1 selected from the group consisting of A298I, S272T+A298V+A369T, V338M+Q382H, L250V+S340G+D399N, S340N, S340V, S340W, H341A, H341C, H341D, H341E, H341F, H341G, H341I, H341K, H341L, H341M, H341N, H341P, H341Q, H341R+G499S, H341S, H341V, H341W, H341Y, D343A, D343E+L562H, R250L+D343E+K494E, D343F, D343H, D343I, D343K, D343L, D343M, D343N+S490S, D343Q, D343R, D343 S, D343W, D343Y, D343V, G352A, G352C, G352D, G352E, G352F, G352I, G352K, G352L, G352M, G352N, G352P, G352Q, G352R, G352S, G352T, G352V, G352W, G352Y, K354A, K354C, K354D, K354E, K354F, K354G, K354H, K354M, M342L+K354N, K354P, K354Q, K354Y, K354R, K354S, G426A, G426C, G426D, G426E, G426F, G426H, G426I, G426K, G426L, G426M, G426N, G426P, G426R, G426S+A578V, G426T, G426W, G426Y, G426V, V431F, F432I, F432K, F432L, F432M, F432Q, F432R, F432T and F432V.

7. An isolated polypeptide having glucose dehydrogenase (GLD) activity, wherein said polypeptide consists of an amino acid sequence having 95% or more identity with SEQ ID NO: 1, wherein said polypeptide comprises at least one substitution at a position corresponding to a position of SEQ ID NO: 1 selected from the group consisting of positions 298, 338, 340, 341, 343, 352, 354, 426 and 431 of SEQ ID NO: 1, and wherein said polypeptide has reduced susceptibility to inhibition by 1,10-phenanthroline, as compared with the polypeptide of SEQ ID NO: 1.

8. The isolated polypeptide according to claim 7, wherein the at least one substitution is one or more selected from the group consisting of:

A298I, A298V, V338M, S340G, S340N, S340V, S340W, H341A, H341C, H341D, H341E, H341F, H341G, H341I, H341K, H341L, H341M, H341N, H341P, H341Q, H341R, H341S, H341V, H341W, H341Y, D343A, D343E, D343F, D343H, D343I, D343K, D343L, D343M, D343N, D343Q, D343R, D343S, D343W, D343Y, D343V, G352A, G352C, G352D, G352E, G352F, G352I, G352K, G352L, G352M, G352N, G352P, G352Q, G352R, G352S, G352T, G352V, G352W, G352Y, K354A, K354C, K354D, K354E, K354F, K354G, K354H, K354M, K354N, K354P, K354Q, K354Y, K354R, K354S, G426A, G426C, G426D, G426E, G426F, G426H, G426I, G426K, G426L, G426M, G426N, G426P, G426R, G426S, G426T, G426W, G426Y, G426V and V431F.

9. The isolated polypeptide according to claim 7, wherein the at least one substitution is one or more selected from the group consisting of:

A298I, S272T+A298V+A369T, V338M+Q382H, L250V+S340G+D399N, S340N, S340V, S340W, H341A, H341C, H341D, H341E, H341F, H341G, H341I, H341K, H341L, H341M, H341N, H341P, H341Q, H341R+G499S, H341S, H341V, H341W, H341Y, D343A, D343E+L562H, R250L+D343E+K494E, D343F, D343H, D343I, D343K, D343L, D343M, D343N+S490S, D343Q, D343R, D343S, D343W, D343Y, D343V, G352A, G352C, G352D, G352E, G352F, G352I, G352K, G352L, G352M, G352N, G352P, G352Q, G352R, G352S, G352T, G352V, G352W, G352Y, K354A, K354C, K354D, K354E, K354F, K354G, K354H, K354M, M342L+K354N, K354P, K354Q, K354Y, K354R, K354S, G426A, G426C, G426D, G426E, G426F, G426H, G426I, G426K, G426L, G426M, G426N, G426P, G426R, G426S+A578V, G426T, G426W, G426Y, G426V and V431F.

10. A reagent composition for determining glucose concentration, comprising the isolated polypeptide of claim 7.

11. A biosensor comprising for determining glucose concentration, comprising the isolated polypeptide of claim 7.

* * * * *